(12) United States Patent
Onishi et al.

(10) Patent No.: US 6,679,436 B1
(45) Date of Patent: Jan. 20, 2004

(54) SPRAYER

(75) Inventors: Yoshihide Onishi, Kyoto (JP); Shinya Tanaka, Kyoto (JP); Masashi Osuga, Kyoto (JP); Takao Terada, Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 09/868,185

(22) PCT Filed: Nov. 29, 1999

(86) PCT No.: PCT/JP99/06665
§ 371 (c)(1),
(2), (4) Date: Jun. 15, 2001

(87) PCT Pub. No.: WO00/37132
PCT Pub. Date: Jun. 29, 2000

(30) Foreign Application Priority Data

Dec. 18, 1998 (JP) ............................. 10-361161

(51) Int. Cl.⁷ .......................... B05B 1/08; A01G 25/00; A01G 27/00
(52) U.S. Cl. ................ 239/101; 239/102.1; 239/102.2; 239/63; 239/67
(58) Field of Search ............................. 239/101, 102.1, 239/102.2, 63, 67, 68–70, 302, 303, 304, 350, 352, 99

(56) References Cited

U.S. PATENT DOCUMENTS

| 4,373,820 | A | * | 2/1983 | Browning ................... 366/101 |
| 4,568,428 | A | * | 2/1986 | Rigg et al. .................... 203/91 |
| 4,799,945 | A | * | 1/1989 | Chang .......................... 62/532 |
| 4,958,747 | A | * | 9/1990 | Sheets ......................... 222/67 |
| 5,741,238 | A | * | 4/1998 | Bradbury et al. ........... 604/322 |
| 5,927,618 | A | * | 7/1999 | Jefferies et al. .......... 239/690.1 |
| 6,056,154 | A | * | 5/2000 | Fowler ........................... 222/1 |

FOREIGN PATENT DOCUMENTS

| DE | 31 22 682 | 12/1982 |
| GB | 2 099 710 | 12/1982 |
| JP | 61-25900 | 8/1986 |
| JP | 2-21079 | 6/1990 |
| JP | 7-231938 | 9/1995 |
| JP | 8-52216 | 2/1996 |
| JP | 8-281165 | 10/1996 |

* cited by examiner

*Primary Examiner*—Davis Hwu
(74) *Attorney, Agent, or Firm*—Morrison & Foerster LLP

(57) ABSTRACT

A spray sprays a liquid medicine from a spray part 30. When a liquid sensing electrode 55, 56 arranged on the spray part 30 senses the quantity of the liquid stored in a storage part 30a and determines that the quantity of the liquid decreases, a pin part 27 is driven by a solenoid 26 for feeding the liquid medicine from a liquid medicine bottle 20 to the storage part 30a of the spray part 30 through a feed pipe 25, and the feeding interval is obtained when the liquid medicine is intermittently fed for adjusting power supplied to a piezo-electric element 50 of the spray part 30 so that the feeding interval is constant. Consequently, a spray capable of automatically adjusting the quantity of spraying per unit time to a constant level for spray liquids having various properties can be provided.

22 Claims, 15 Drawing Sheets

Figure 1:
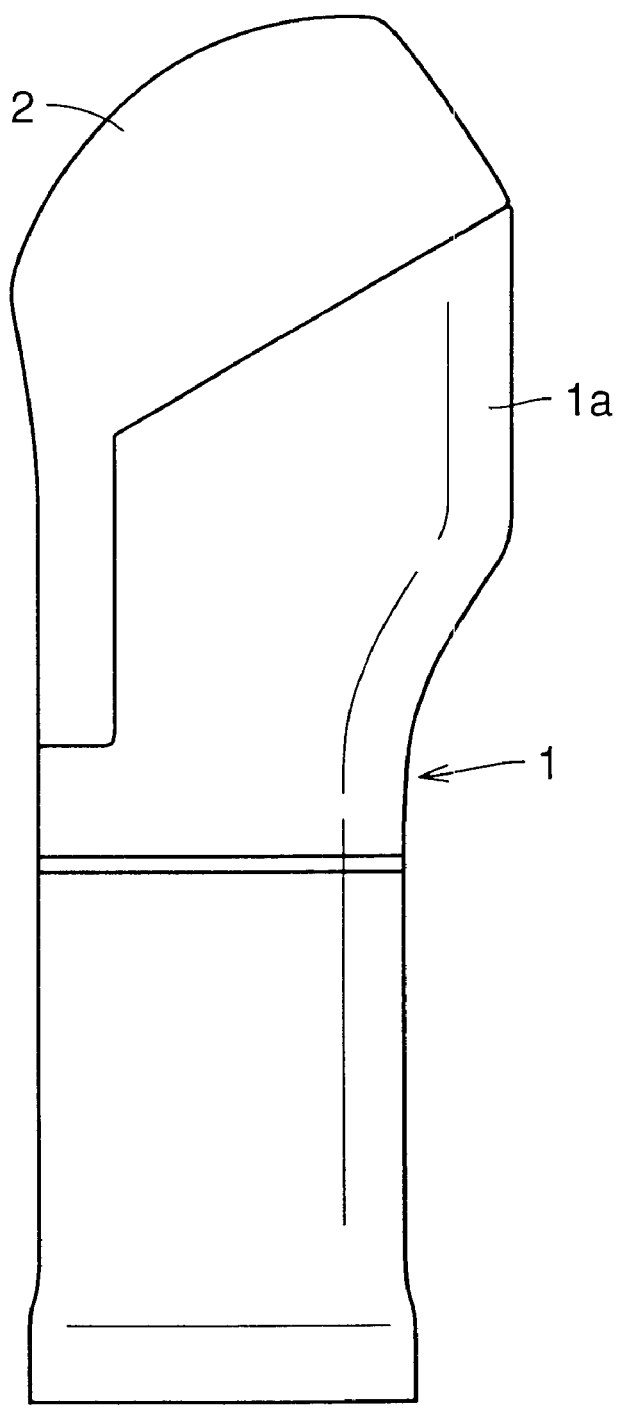
Figure 2:
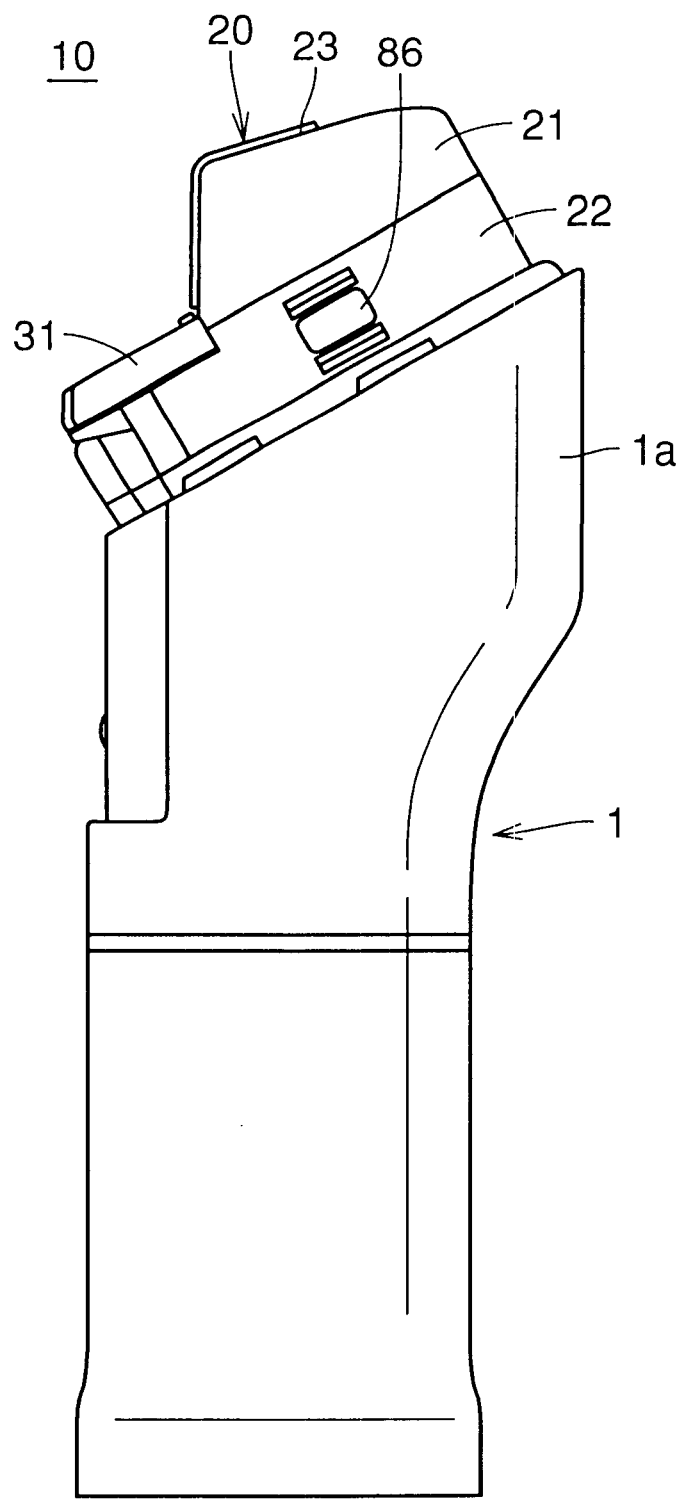
Figure 3:
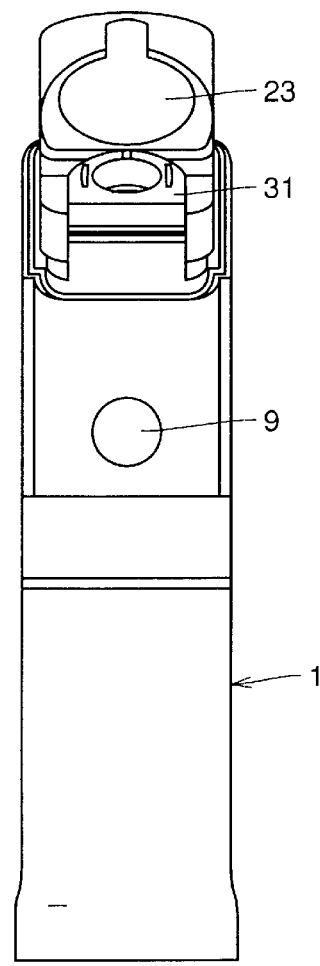
Figure 4:
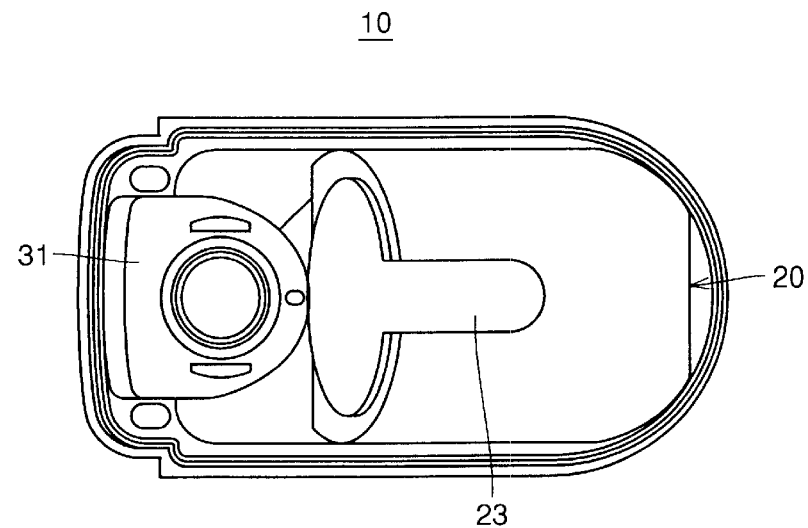
Figure 5:
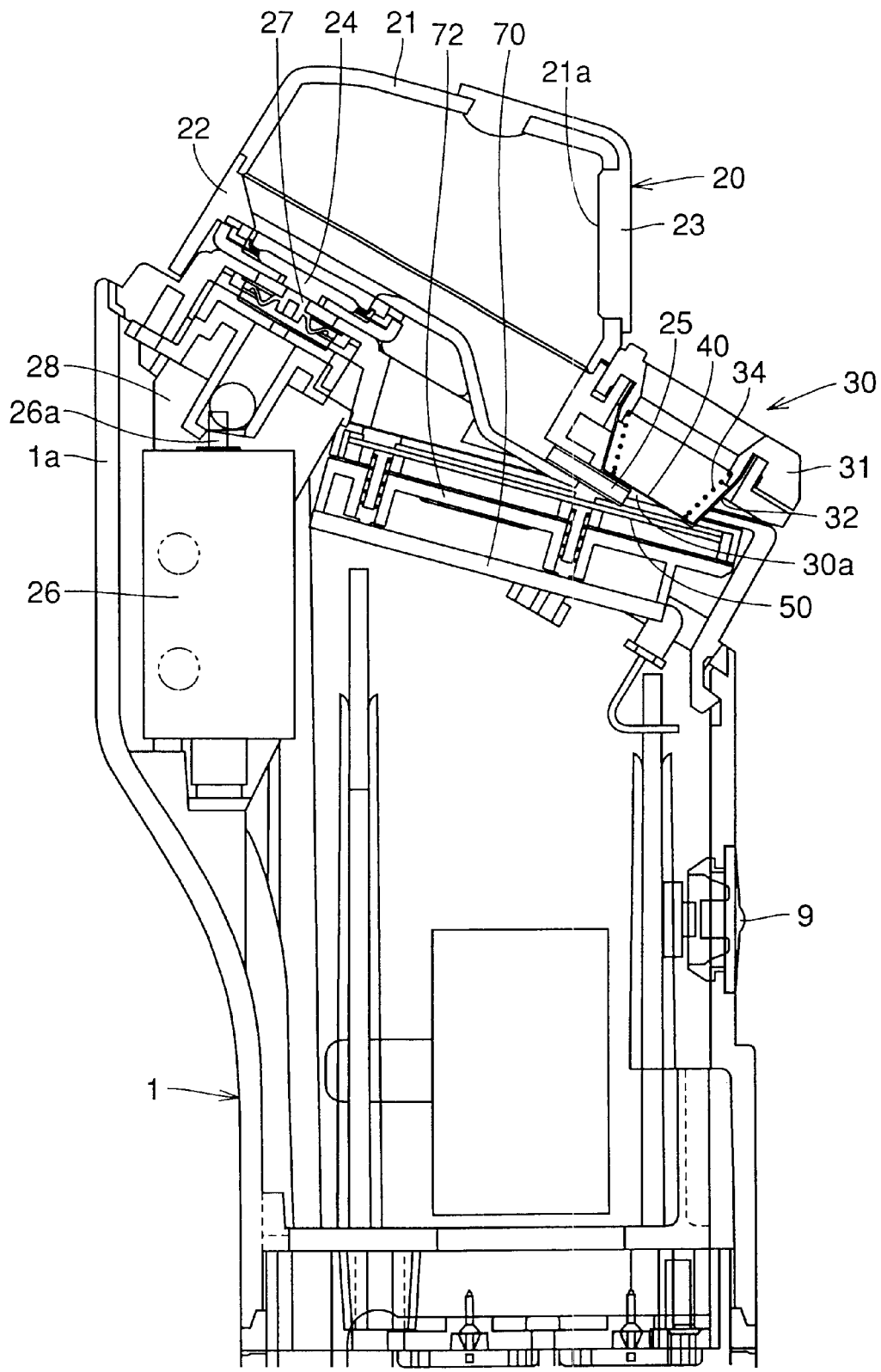
Figure 6A:
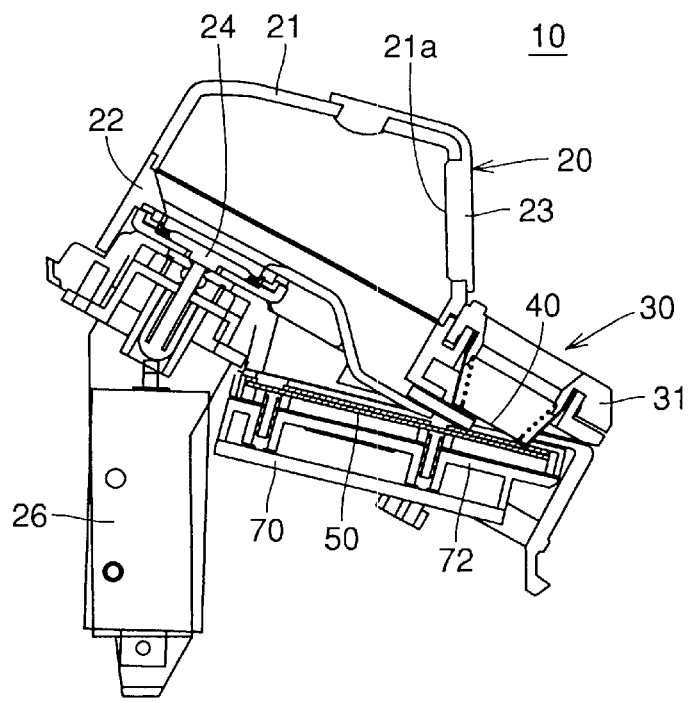
Figure 6B:
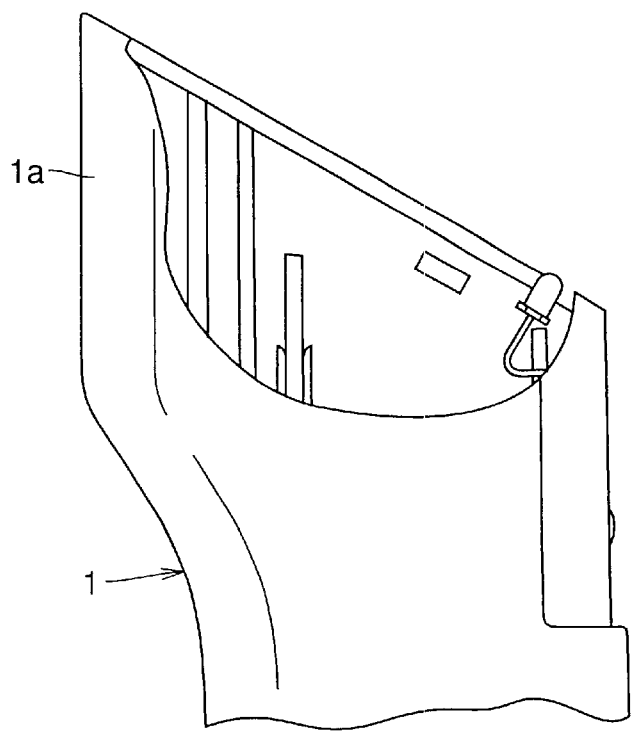

DIRECTION
WHERE
LIQUID
DECREASES
→

INPUT

OUTPUT

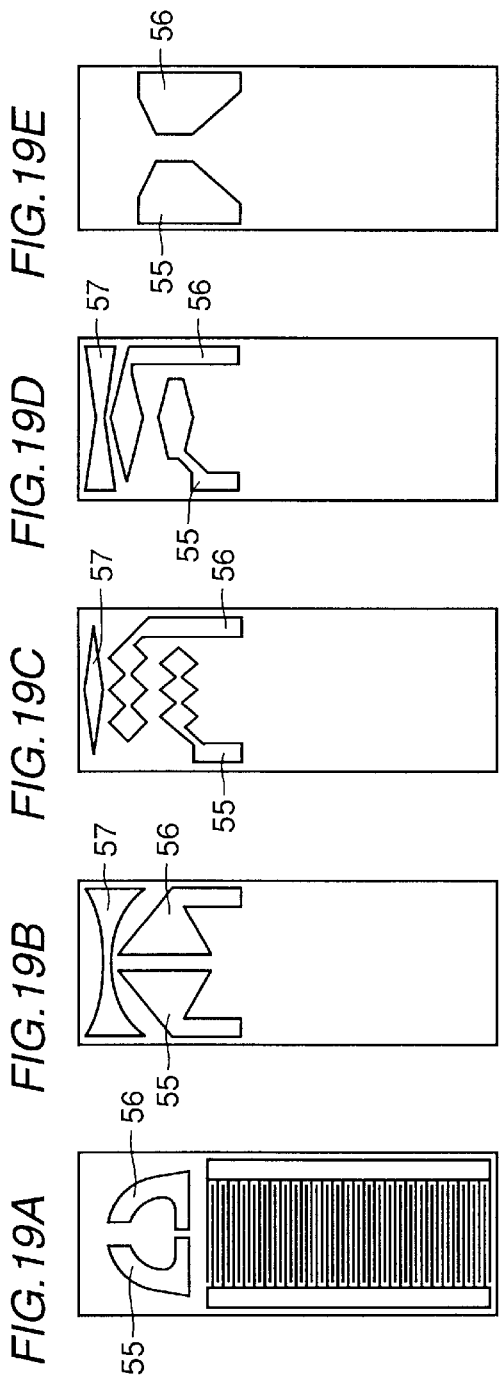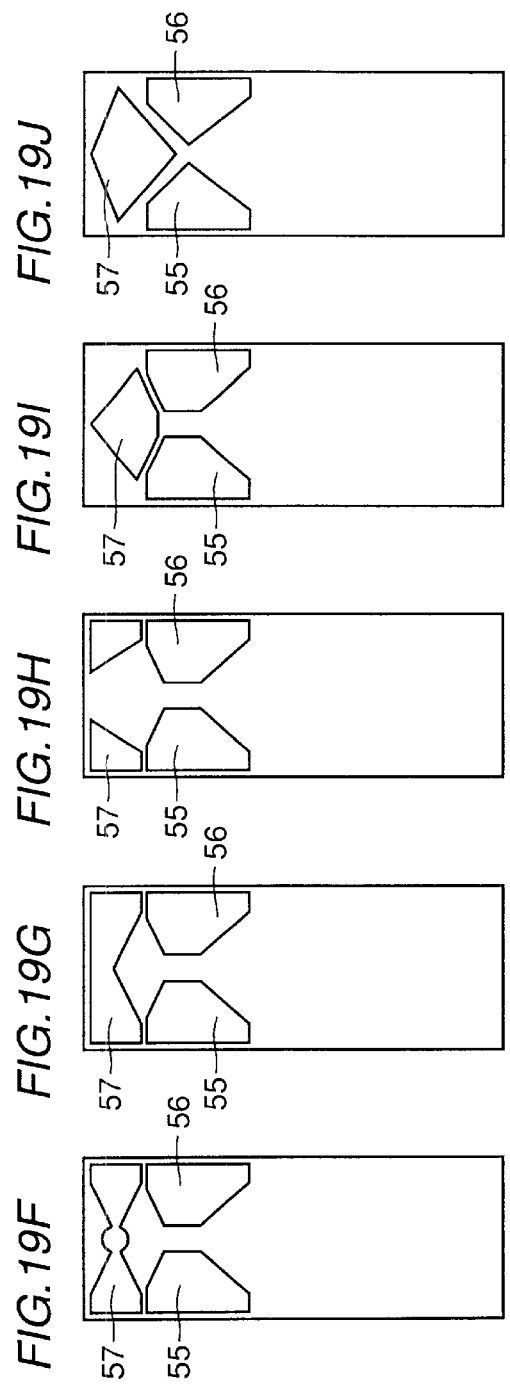

— SPRAYER —

TECHNICAL FIELD

The present invention relates to a spray of an inhaler.

BACKGROUND TECHNIQUE

In general, sprays of inhalers or the like include a spray feeding a liquid medicine from a storage part such as a liquid medicine tank to a spray part formed by the vibrating surface of an oscillator and atomizing the liquid medicine. This type of spray is provided with a function enabling the user to manually adjust the quantity of spraying, or the quantity of spraying is adjusted in response to the application of the spray when the spray is shipped from a factory, thereby implementing the optimum quantity of spraying.

In a medical inhaler employed for treating or preventing a disease such as asthma, various types of liquid medicines, i.e., spray liquids may be used depending on the state of the disease of the patient. An optimum quantity of spraying is present for the medical inhaler since the patient is choked by spraying and cannot readily inhale the liquid medicine if the quantity of spraying is too large while the time for spraying the liquid medicine is increased to increase the time for treating and restricting the patient if the quantity of spraying is too small. Sprayability varies with the property of the spray liquid, and hence the patient generally has to manually adjust the quantity of spraying to an optimum level in response to the quantity of spraying for each spray liquid or put up with a quantity of spraying larger or smaller than the optimum quantity of spraying when the spray has no function for adjusting the quantity of spraying. When the sprayability of the conventional spray is reduced by abnormality (excessive deterioration, failure or the like) of the apparatus, it takes time for the user to notice the abnormality since the spray has no means for determining the state thereof.

The present invention has been proposed in consideration of the aforementioned problems, and an object thereof is to provide a spray which can automatically adjust the quantity of spraying per unit time to a constant level with respect to spray liquids of various properties, by adjusting power supplied to a spray part so that an interval for feeding a liquid to the spray part is constant. Another object of the present invention is to provide a spray monitoring the state of spraying for immediately posting abnormality of spraying to the user when the abnormality is detected.

DISCLOSURE OF THE INVENTION

The spray according to the present invention comprises a first storage part and a second storage part for storing a spray liquid, a spray part spraying the spray liquid stored in the second storage part, a feeding part feeding a constant quantity of spray liquid from the first storage part to the second storage part, a liquid sensing part detecting presence/absence or increase/decrease of the spray liquid in the second storage part and a feeding determination part for determining whether or not the second storage part requires feeding of the liquid, and adjusts power supplied to the spray part so that the spray liquid is fed to the second storage part at a prescribed interval.

Consequently, the quantity of spray liquid fed to the second storage part per dose can be automatically adjusted to a constant level.

In the spray according to the present invention, utilizing oscillation of an oscillator, a self-excited oscillation circuit utilizing the resonance of the oscillator is formed as a driving circuit for the oscillator, an element such as a coil having a high impedance in an inserted oscillation frequency band is inserted into the side of a GND line in order to separate the oscillator driving circuit and a power supply part from each other, and a circuit rectifying and smoothing an oscillator driving frequency current and converting the current to a voltage is added for monitoring a state of atomization.

BRIEF DESCRIPTION OF THE DRAWINGS

FIG. 1 is a side elevational view of a medical inhaler according to an embodiment of the present invention.

FIG. 2 is a side elevational view showing a state where a cover is detached from a body case of the medical inhaler.

FIG. 3 is a front elevational view of the inhaler shown in FIG. 2.

FIG. 4 is a top plan view of the inhaler shown in FIG. 2.

FIG. 5 is a sectional view showing a principal part of the inhaler.

FIGS. 6A and 6B are side elevational views showing the state where the cover is detached from the body case of the inhaler.

FIG. 7 is a perspective view showing a piezoelectric element and a circuit substrate employed for the inhaler.

FIG. 8 is a perspective view showing the piezoelectric element employed for the inhaler.

FIG. 9 is a flow chart for illustrating control processing of the inhaler.

FIG. 10 is a diagram showing the frequency-impedance characteristics of the piezoelectric element employed for the inhaler.

FIGS. 11A to 11C are diagrams for illustrating liquid decrease and liquid sensing in a spray part of the inhaler.

FIGS. 12A and 12B are diagrams for illustrating sensing of presence/absence of a liquid in the spray part of the inhaler.

FIGS. 13A and 13B are waveform diagrams for illustrating noise removal in the inhaler.

FIG. 14 is a circuit diagram showing a piezoelectric element driving circuit of the inhaler.

FIG. 15 is a diagram illustrating the timing of liquid sensing in the inhaler.

FIGS. 16A and 16B are diagrams showing another exemplary liquid sensing electrode employable for the inhaler.

FIG. 17 is a diagram showing still another exemplary liquid sensing electrode employable for the inhaler.

FIG. 18 is a flow chart for illustrating another control processing employable for the inhaler.

FIGS. 19A to 19J are diagrams showing other exemplary shapes of the liquid sensing electrode employable for the inhaler.

FIGS. 20A to 20D are diagrams showing other exemplary piezoelectric element holding structures employable for the inhaler.

BEST MODE FOR CARRYING OUT THE INVENTION

An embodiment of the present invention is now described in detail with reference to the drawings. Referring to FIGS. 1 to 6B showing a medical inhaler (spray) according to the embodiment, the spray comprises a prismatic body case (body part) 1 and a cover 2 detachably mounted on the body case 1. The body case 1 has a backwardly protruding projection 1a provided on the back surface of the upper portion of the body case 1 and an operation switch 9 for turning on/off a power source provided on the front surface of the upper portion corresponding to the projection 1a.

When the cover 2 is detached from the body case 1, a body cover part 10 appears on the upper portion of the body case 1, and the body cover part 10 is attachable to/detachable from the body case 1, while a piezoelectric element 50 described later, a mesh member 40, storage parts and a feeding part are arranged on the body cover part 10.

The body cover part 10 has a liquid medicine bottle 20 defining a first storage part storing a liquid (a liquid medicine, for example), and the liquid medicine bottle 20 is formed by an upper part 21 and a lower part 22. The upper and lower parts 21 and 22 engage with each other, and a cap body 23 for sealing up a liquid medicine injection port 21a is mounted on the upper part 21 in an openable/closable manner, so that the liquid medicine can be introduced into the liquid medicine bottle 20 from the liquid medicine injection port 21a by opening the cap body 23. A diaphragm 24 is mounted on the bottom portion of the liquid medicine bottle 20 (lower part 22), and a feed pipe 25 is mounted on an inclined lower portion of the lower part 22.

A solenoid 26 for pressing the diaphragm 24 is arranged under the liquid medicine bottle 20. The solenoid 26 is mounted on a solenoid holding part 28, so that a solenoid shaft 26a pushes a pin part 27. The pin part 27 is in contact with the diaphragm 24 in a normal state. When the solenoid 26 operates, therefore, the solenoid shaft 26a pushes the pin part 27 and the pin part 27 presses the diaphragm 24, so that a proper quantity of liquid medicine is discharged from the liquid medicine bottle 20 through the feed pipe 25. The feed pipe 25, the solenoid 26, the pin part 27 etc. form the feeding part.

According to this liquid medicine feeding structure, the optimum quantity of liquid medicine can be fed by properly setting the quantity of displacement of the diaphragm 24 pressed by the pin part 27, so that inconvenience such as clogging can be prevented.

The pin part 27 may alternatively be operated with a motor or by pneumatic pressure, in place of the solenoid 26.

A spray part 30 is arranged on the lower part 22 of the liquid medicine bottle 20. The spray part 30 includes an upper case 31 and a lower case 32, which engage with each other to form a mesh member case. The mesh member 40 having a number of pores is arranged on the lower case 32, while a coiled spring 34 is provided for pressing the mesh member 40 against the lower case 32. The spring 34 has an end engaging with the upper case 31 and another end engaging with the periphery of the mesh member 40. Therefore, the mesh member 40 is regularly pressed against and held on the lower case 32. The mesh member 40 is made of a metal or ceramic. This is for suppressing absorption of vibrational energy propagating the liquid medicine and improving the effect of spraying while improving strength against an impact caused when the body cover part 10 is dropped or the like. When sprayed, the liquid medicine comes into contact with the mesh member 40, and simultaneously comes into contact also with the mesh member case (the upper and lower cases 31 and 32) holding the mesh member 40. In general, such a mesh member case is made of resin, to disadvantageously damp vibration of the liquid medicine and the mesh member. This problem can be solved by preparing the mesh member case from a metal or ceramic.

Under the mesh member 40 obliquely positioned with respect to the horizontal plane, the piezoelectric element 50 described later is similarly obliquely located in proximity thereto. Opposing surfaces of the mesh member 40 and the piezoelectric element 50 acutely intersect with each other, so that the liquid medicine received from the feed pipe 25 is fed through openings of the mesh member 40 and the piezoelectric element 50. The space between the mesh member 40 and the piezoelectric element 50 defines a second storage part 30a.

A liquid quantity sensing part for sensing the quantity of the liquid medicine is provided on the piezoelectric element 50, for controlling the operation for pressing the diaphragm 24 on the basis of an output from this liquid quantity sensing part. This feature is described later in detail.

Figure 7:
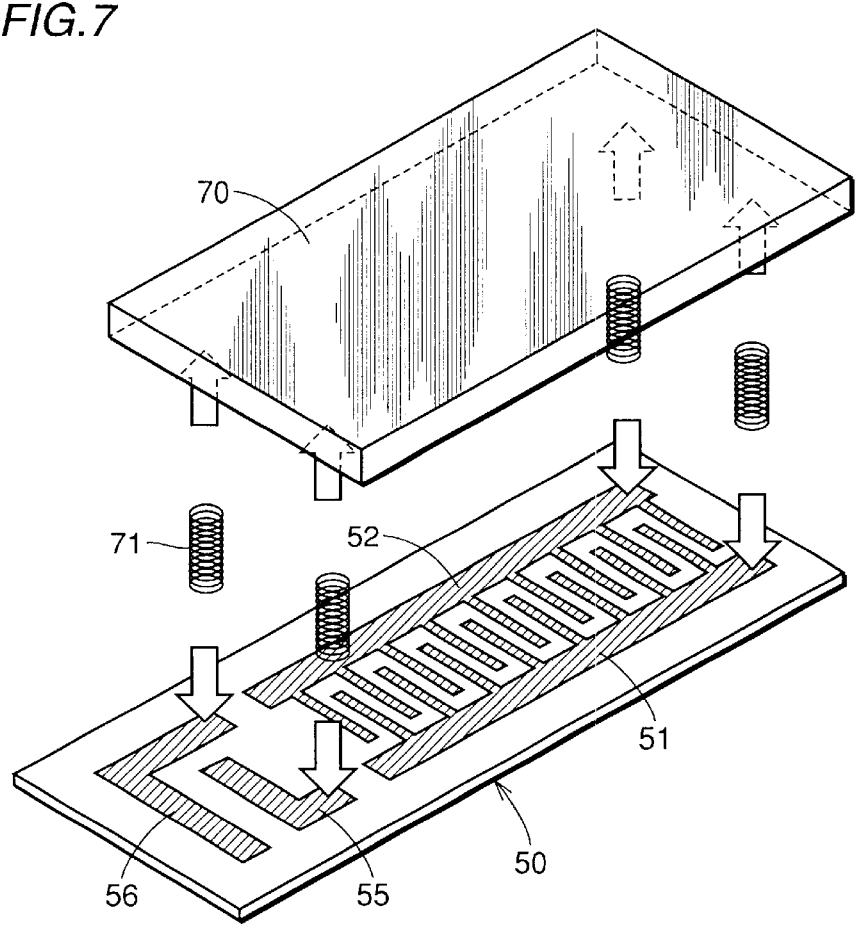
Figure 8:
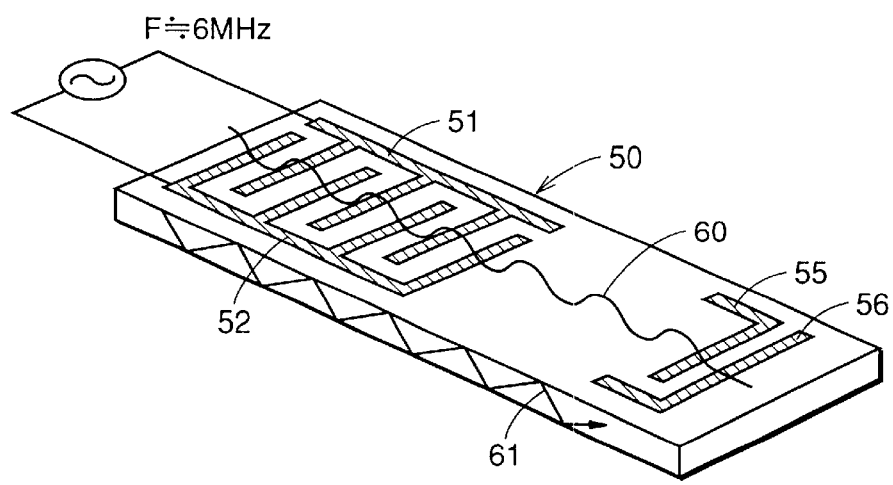

As shown in FIGS. 7 and 8, the piezoelectric element 50 has interdigital electrodes including a first electrode 51 and a second electrode 52 alternately formed on a single surface and liquid sensing electrodes 55 and 56 for sensing the liquid medicine formed on the same surface on positions coming into contact with the liquid medicine fed from the feed pipe 25. The piezoelectric element 50 is so arranged that a surface (non-electrode forming surface) opposite to the surface formed with the electrodes 51, 52, 55 and 56 is opposed to the mesh member 40. This is because the oscillatory wave of the piezoelectric element 50 employed for atomization is not a surface wave 60 dissimilarly to the prior art but a bulk wave 61 passing through the inner part of the piezoelectric element 50. The non-electrode forming surface of the piezoelectric element 50 is so opposed to the mesh member 40 that the liquid medicine is not in contact with the electrodes but the electrodes can be protected against corrosion, electric corrosion and electric shorting caused by the liquid medicine and the spray is improved in reliability.

While the material for the piezoelectric element 50 is not particularly restricted, lithium niobate is preferably employed as the material with a 41 ±15° rotation Y-cut plane and a propagation direction of Y-axis projection since the spray utilizes the bulk wave as the oscillatory wave as described later.

The peripheral end portion of the piezoelectric element 50 is compressed and held by a waterproof packing (not shown). In the piezoelectric element 50, the part formed with the interdigital electrodes 51 and 52 vibrates while vibration of the peripheral end portion is smaller than that of the part formed with the electrodes. Therefore, periodic damping of the piezoelectric element 50 can be minimized by compressing and holding only the peripheral end portion of the piezoelectric element 50. Further, the liquid medicine fed to the non-electrode forming surface of the piezoelectric element 50 flows downward from the piezoelectric element 50, so that the inner part of the spray can be prevented from corrosion, deformation, discoloration and the like by the waterproof packing.

A substrate 70 loaded with circuits such as a liquid sensing circuit, a piezoelectric element driving circuit, a control CPU and the like is arranged under the electrode forming surface of the piezoelectric element 50, and this circuit substrate 70 is electrically connected with the interdigital electrodes 51 and 52 and the liquid sensing electrodes 55 and 56 of the piezoelectric element 50 by conductive coil springs (elastic bodies) 71.

Vibrational operation of the piezoelectric element 50 is now described. When an alternating current of 6 MHz in frequency, for example, is fed to the electrodes 51 and 52 of the piezoelectric element 50, the surface wave (surface acoustic wave) 60 passing through the surface and the bulk wave 61 passing through the inner part are generated. That is, the piezoelectric element 50 converts electric energy to vibrational energy, and more specifically, the electrodes 51 and 52 convert electric energy to mechanical vibrational energy.

In this piezoelectric element 50, the vibration source is defined by the alternately formed interdigital electrodes 51 and 52, and generated oscillatory waves are the surface wave 60 and the bulk wave 61. The bulk wave 61 obliquely propagates through the inner part with respect to the longitudinal direction of the piezoelectric element 50, and assuming that represents the normal direction of the equiphase wave surface of the excited bulk wave, θ is given by the following equation and the traveling direction of the bulk wave varies with the frequency:

$$\theta = \sin(Vb/P \cdot f)$$

where Vb represents the phase velocity of the bulk wave, P represents the pitch of the interdigital electrodes 51 and 52, and f represents the frequency.

The bulk wave propagates while being reflected by the boundary surface of the piezoelectric element 50. While the vibrational frequency of the surface wave excited by the interdigital electrodes 51 and 52 is mainly decided by the sound velocity Vs of the surface wave and the pitch P, the vibrational frequency of the bulk wave is decided by the thickness t of the piezoelectric element 50.

In general, a liquid medicine optimum for treatment or prevention is prescribed for a medical inhaler in response to the degree of the disease of the patient. Such liquid medicines have various properties requiring different sprayability levels, and hence the quantity of spraying per unit time varies with the liquid medicines. In the inhaler according to this embodiment, the spray liquid is introduced into the liquid medicine bottle 20 defining the first storage part in a quantity necessary and sufficient for attaining an effect of treatment or prevention. When the quantity of the liquid fed from the first storage part 20 to the second storage part 30a per dose is constant, the quantity of spraying per unit time can be controlled to the optimum value by adjusting power supplied to the spray part 30 so that the liquid is fed at a constant interval. The quantity of spraying per unit time is calculated as follows:

(quantity of spraying per unit time)=(quantity of feeding per dose)/(feeding interval)

Figure 9:
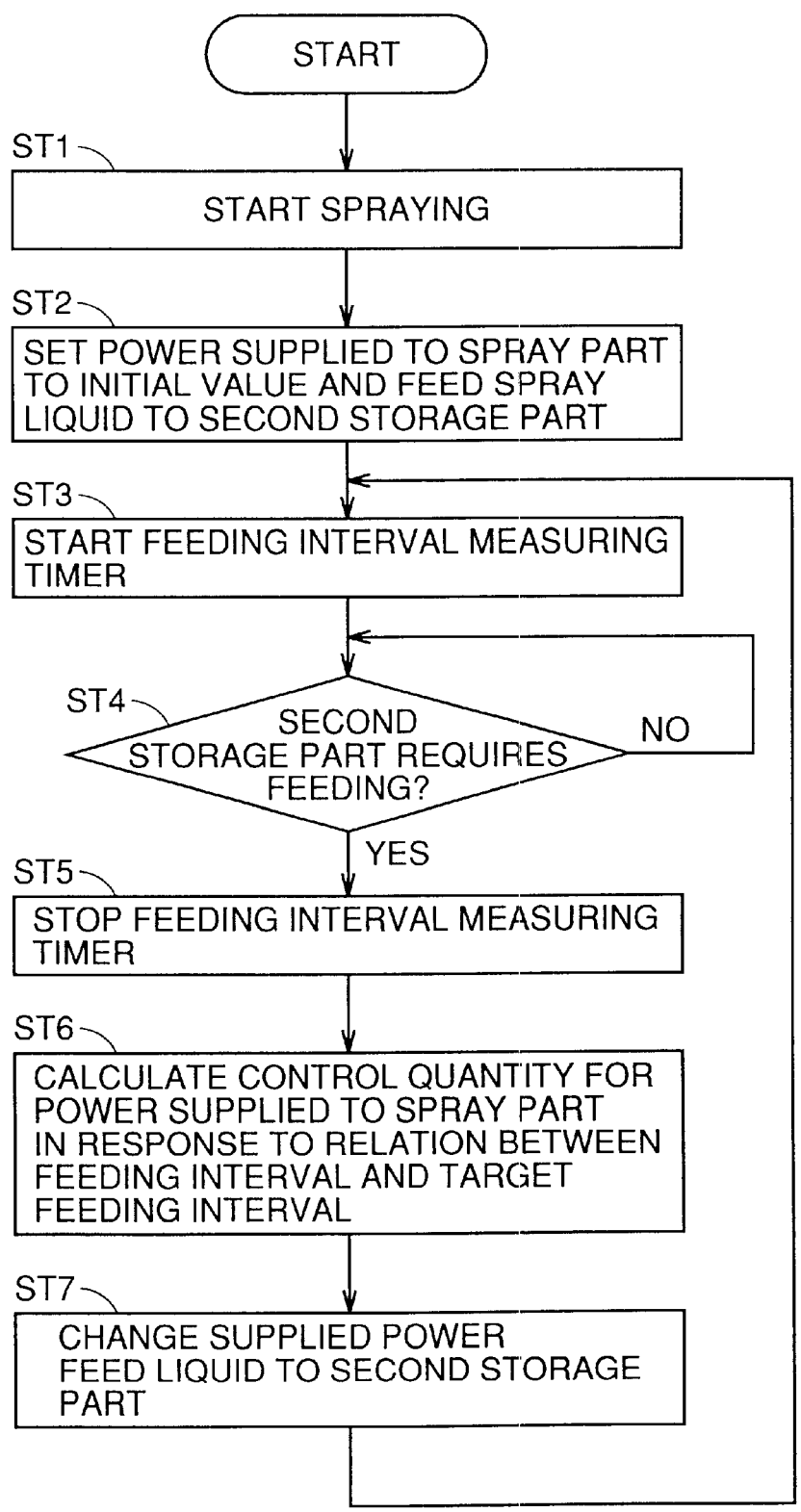

Thus, it is understood possible to adjust the quantity of spraying per unit time to a constant level by feeding the liquid at a constant interval. In the inhaler according to this embodiment, processing of a flow chart shown in FIG. 9 is performed for automatically adjusting the quantity of spraying per unit time to a constant level.

When spraying is started (ST1), the power supplied to the spray part is set to an initial value, while the liquid is fed from the first storage part 20 to the second storage part 30a (ST2). A feeding interval measuring timer is started at the same time (ST3). Then, the quantity of the liquid stored in the second storage part 30a is sensed for determining whether or not the second storage part 30a requires feeding, i.e., whether or not the flow rate is insufficient (ST4). If no feeding is necessary, the operation is maintained as such. When feeding is determined as necessary at the step ST4, the feeding interval measuring timer is stopped (ST5), a control quantity for the power supplied to the spray part is calculated in response to the relation between the feeding interval and a target feeding interval (ST6) for changing the supplied power while feeding the liquid to the second storage part 30a (ST7), and the process returns to the step ST3. The power supplied to the spray part 30 is increased if the feeding interval measured by the timer is longer than the target feeding interval, while the supplied power is reduced if the former is shorter than the latter.

While the piezoelectric element 50 of the inhaler according to this embodiment having the liquid sensing electrodes 55 and 56 shown in FIG. 7 is influenced by an impedance component of the spray liquid when the liquid sensing electrodes directly come into contact with the spray liquid and the operation of the liquid sensing circuit is unstabilized in application to a medical inhaler or the like employing spray liquids of various properties, the liquid sensing electrodes 55 and 56 are formed on the surface opposite to the part storing the spray liquid and not directly in contact with the liquid medicine according to this embodiment, and hence the liquid can be stably sensed regardless of the property of the liquid medicine. The liquid sensing electrodes 55 and 56 are connected with the liquid sensing circuit by the conductive elastic bodies 71 for preventing the piezoelectric element from periodic damping. The piezoelectric element 50 also has the interdigital electrodes including the alternately formed first and second electrodes 51 and 52 as driving electrodes, and the interdigital electrodes are also connected with the piezoelectric driving circuit by the conductive elastic bodies 71.

Figure 10:
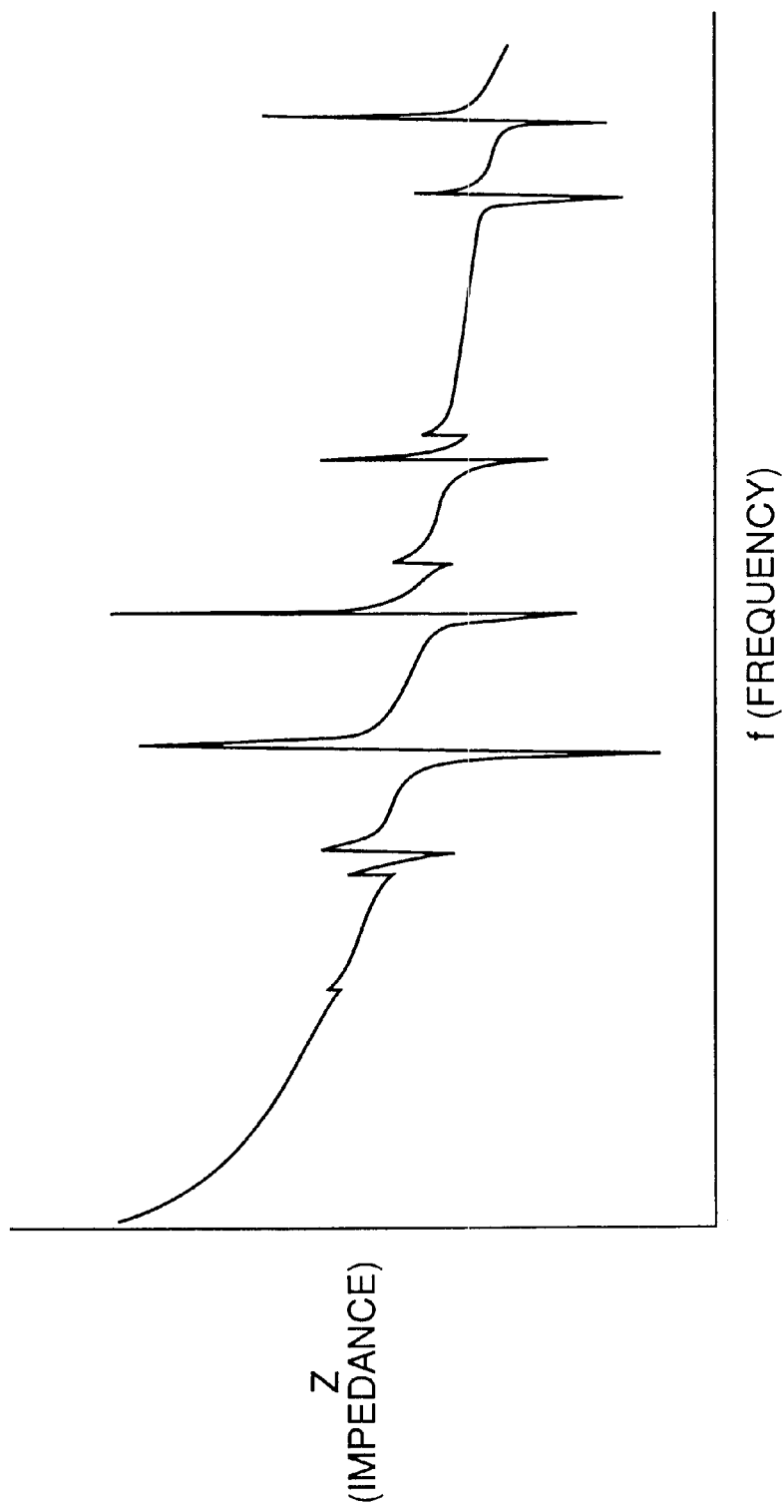

The piezoelectric element 50 employed in this embodiment has a number of resonance frequencies specifically decided in response to the size thereof and the shapes of the electrodes, as shown in FIG. 10. When the spray liquid is collected in the second storage part 30a, the impedance across the liquid sensing electrodes changes to change the resonance state. Liquid sensing can be stably implemented by forming an oscillation circuit utilizing this resonance characteristic as the liquid sensing circuit and detecting whether or not the liquid medicine is present on the liquid sensing electrodes by detecting change of the oscillation frequency and starting and stoppage of oscillation.

Figure 11C:
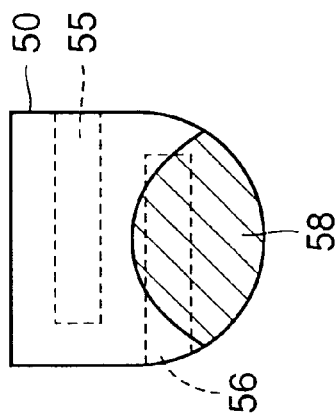
Figure 11B:
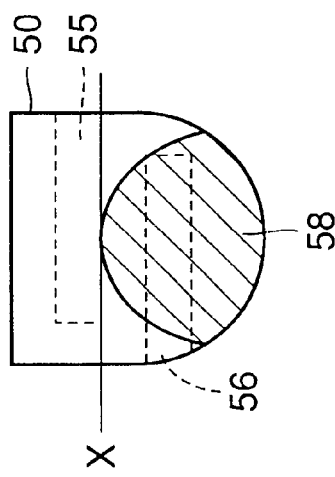
Figure 11A:
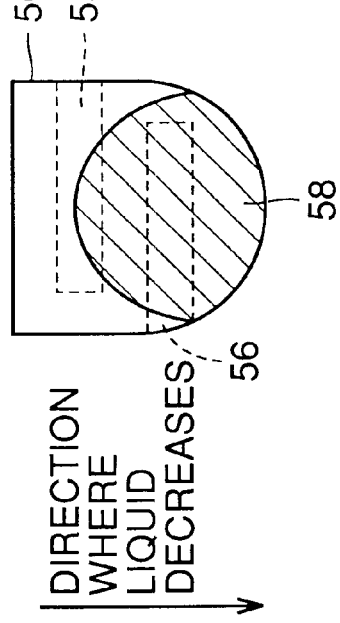
Figure 12A:
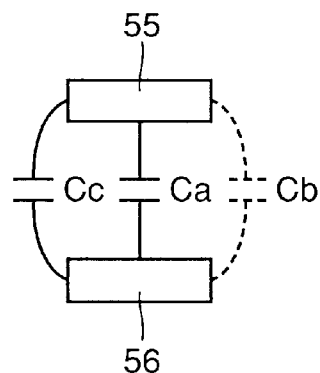
Figure 12B:
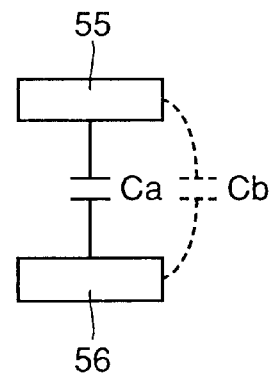

In the inhaler according to this embodiment, the piezoelectric element 50 utilized as the spray part is arranged to be inclined with respect to the horizontal plane, so that the liquid medicine 58 stored in the second storage part decreases from a high position toward a low position. While the liquid must be fed before the spray liquid (liquid medicine) 58 completely runs out in order to keep the quantity of spraying constant, the feeding timing can be sensitively set by arranging the liquid sensing electrodes in positional relation shown in FIGS. 11A to 11C, for example. The spray liquid generally has a large dielectric constant as shown in FIGS. 12A and 12B, and hence the electrostatic capacitance of the spray liquid across the two electrodes remarkably changes when the spray liquid changes from a state (FIGS. 11A and 12A) filling up the space between the electrodes to a state (FIGS. 11C and 12B) not filling up the space between the electrodes. In this case, the electrostatic capacitance across the liquid sensing electrodes is several to several 10 pF and remarkably influenced by floating capacitance and dispersion of the liquid sensing circuit, and hence the liquid sensing electrodes are effectively brought into shapes most remarkably changing at the liquid sensing timing as described above. In other words, stable liquid sensing timing can be implemented by arranging two liquid sensing electrodes in parallel with each other perpendicularly to the direction where the liquid decreases. Further, the liquid sensing timing can also be arbitrarily set by adjusting the positions of the liquid sensing electrodes. In relation to the electrostatic capacitance across the sensing electrodes 55 and 56, a CR oscillator is formed and an output of this CR oscillator is counted by a counter for sensing liquid decrease from change of the count value responsive to frequency change caused by change of the electrostatic capacitance.

Also when change of the electrostatic capacitance across the liquid sensing electrodes is utilized for the liquid sensing circuit, a capacitance detection part generally converts the capacitance to a frequency as described above, and the liquid sensing circuit is generally formed by a frequency output. When the output frequency of the liquid sensing circuit approaches the driving (vibrational) frequency of the piezoelectric element, the frequencies interfere with each other to hinder stable operation. In the inhaler according to this embodiment, therefore, the frequencies are set to sufficiently separated bands for stabilizing the operation.

In general, a piezoelectric element driving circuit is formed to drive a piezoelectric element at a resonance point having the lowest impedance. Therefore, piezoelectric element driving noise is caused at integral times the driving frequency, and the piezoelectric element is remarkably influenced by the noise if the output frequency of the liquid sensing circuit is higher than the piezoelectric element driving frequency. In the inhaler according to this embodiment, therefore, the frequency band of the liquid sensing circuit is formed by a low-frequency band sufficiently lower than the piezoelectric element driving frequency with small noise and no resonance point specific to the piezoelectric element shown in FIG. 10, for stabilizing liquid sensing.

Figure 13A:
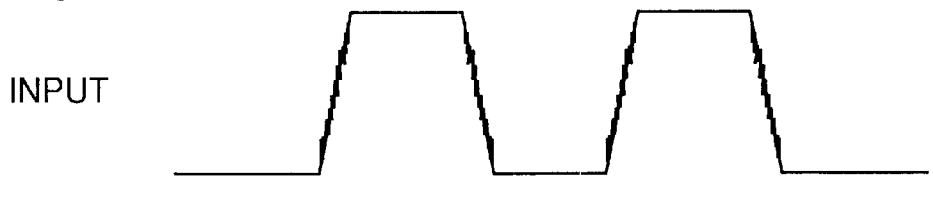
Figure 13B:
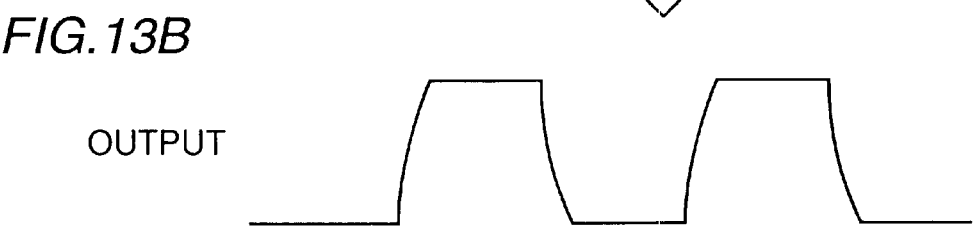

While noise of the piezoelectric element driving frequency may be introduced as shown in FIG. 13A also when the output frequency of the liquid sensing circuit is sufficiently reduced as compared with the piezoelectric element driving frequency, the frequency bands are sufficiently separated from each other and hence a stable output can be readily obtained from the liquid sensing circuit by adding an LPF circuit formed by a capacitor C and a resistor R to the output.

Figure 15:
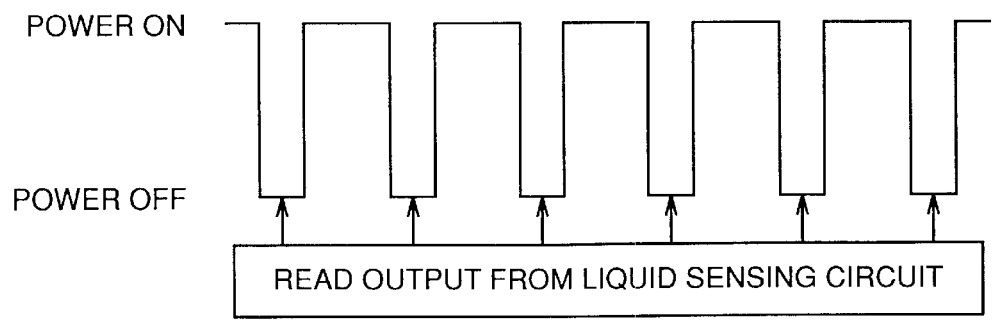

The piezoelectric element driving frequency noise may come into question. In this case, power supply to the piezoelectric element driving circuit is periodically stopped as shown in FIG. 15 in addition to separation of the frequency bands and addition of the LPF (Low Pass Filter) for determining liquid sensing on the basis of the output from the liquid sensing circuit in the period stopping driving the piezoelectric element, so that no noise is caused in the liquid sensing circuit but the liquid can be stably sensed.

The quantity of spraying may be automatically adjusted by a method of changing the voltage or current supplied to the piezoelectric element driving circuit itself or a pulse control method of controlling the quantity of spraying by changing the ratios of an ON state and an OFF state as in PWM (Pulse Width Modulation) control, for example, while keeping the supplied voltage (current) constant. In the inhaler according to this embodiment, pulse control is so employed that the liquid sensing function can also be stabilized in addition to the function of adjusting the quantity of spraying, whereby a simple system can be formed at a low cost.

The spraying is stopped during the period when driving of the piezoelectric element is stopped. When this stop period is sufficiently shortened, the user does not feel that spraying is periodically stopped but can inhale the liquid medicine with no feeling of misfit. The optimum quantity of spraying for a medical inhaler is about 0.3 ml per minute, and if the spraying stop period exceeds about 15 ms in the case of this degree of quantity of spraying, the user feels that atomization is stopped. When the stop period is set to not more than 15 ms, therefore, the user can inhale the liquid medicine with no feeling of misfit.

Figures 16A, 16B:
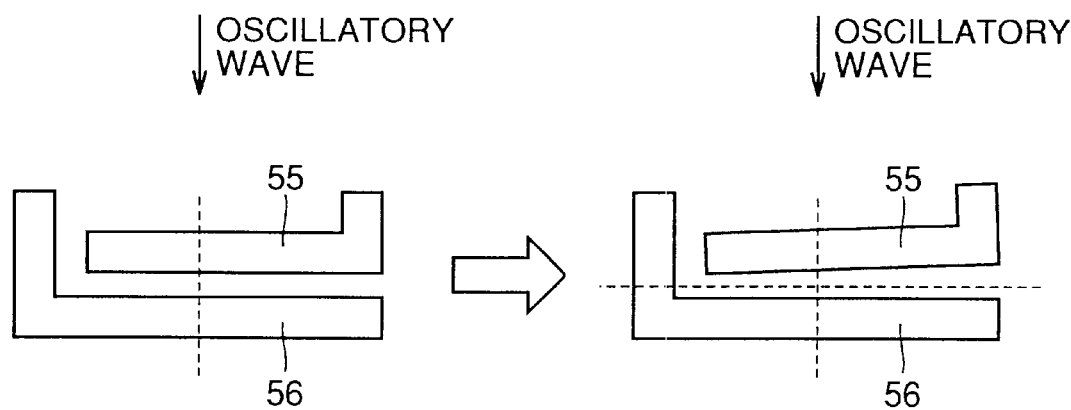

As hereinabove described, stable liquid sensing can be implemented by arranging two liquid sensing electrodes in parallel with each other perpendicularly to the direction where the liquid decreases. Thus, the liquid sensing electrodes have the optimum direction for sensing the liquid, while this direction may be perpendicular to the oscillatory wave of the piezoelectric element as shown in FIG. 8. When the direction is perpendicular to the oscillatory wave, however, it follows that piezoelectric element vibrational frequency noise most remarkably appears on the liquid sensing electrodes. Consequently, noise of the liquid sensing circuit is increased, or the liquid sensing electrodes serve as antennas exerting bad influence of increasing radiation noise when the liquid sensing electrodes have high impedances. In order to reduce this bad influence, the liquid sensing electrodes may be intentionally inclined from the vertical direction, as shown in FIG. 16B.

Figure 17:
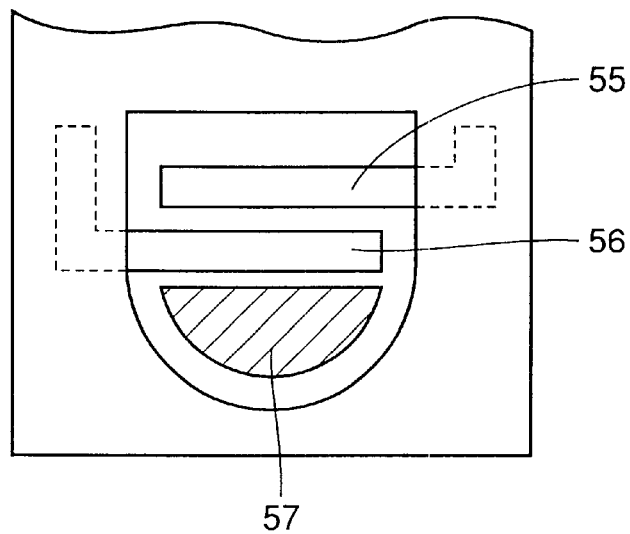

While the fed spray liquid is stored in the second storage part provided on the surface of the piezoelectric element opposite to the liquid sensing electrodes, radiation noise of the piezoelectric element driving frequency is generated through this spray liquid. The radiation noise is increased particularly when the spray liquid contains a physiological salt solution having high conductivity or the like. In order to reduce this radiation noise, an electrode to be connected to a circuit GND 57 having a low impedance or the like may be provided independently of the liquid sensing electrodes, as shown in FIG. 17. The spray liquid and the circuit GND are capacitively connected with each other through the piezoelectric element, so that a high-frequency (piezoelectric element driving frequency) impedance of the spray liquid is consequently reduced so that the radiation noise can be reduced.

This effect is also attained by connecting at least one of the plurality of electrodes for liquid sensing to a fixed potential having a low impedance for forming the liquid sensing circuit, as a matter of course.

When the fixed electrode is not completely perpendicularly arranged but slightly inclined with respect to the direction of the oscillatory wave of the piezoelectric element caused by driving the piezoelectric element, the effect is further improved as described above.

When the spray is applied to a medical inhaler, the quantity of the liquid fed per dose is about 2 to 3 ml, and the optimum quantity of spraying per optimum unit time is about 0.3 ml/min. When the quantity of the spray liquid is 2 ml, therefore, the total spraying time is about 7 minutes. When the quantity of the liquid fed to the second storage part 30*a* per dose is 100 $\mu$l, the time required for spraying the liquid by 100 $\mu$l is about 20 seconds. According to the present invention, the second storage part 30*a* is controlled to spray the spray liquid at a constant interval, and hence a delay of the control comes into question if this time is too long. Assuming that the quantity of spraying can be controlled around the optimum unit quantity of spraying by changing the control value about three times, the quantity of spraying is stabled after a lapse of about one minute, and this degree is the limit considering that the minimum total spraying time is about 7 minutes. If the quantity of feeding is too small, however, it is difficult to control the quantity of feeding and hence the quantity of feeding is preferably set to 50 $\mu$l, i.e., a quantity sprayable within a period of about 10 seconds in consideration of balance with the control.

In order to eliminate the aforementioned delay of control, the control may be started by setting the power to the spray part to the maximum value. The spray liquid fed to the second storage part quickly runs out as the power is increased so that next control power can be quickly decided, whereby the quantity of spraying can be quickly converged to the target unit quantity of spraying.

In the inhaler automatically adjusting the quantity of spraying, the quantity of spraying per unit time is controlled substantially constant in any apparatus and hence it is difficult to grasp the sprayability of the apparatus in a step of inspecting the apparatus at the time of manufacturing. While the sprayability can be roughly determined from the relation between power applied to the spray and the quantity of spraying in practice, it follows that an error is caused in correspondence to the aforementioned delay of control when the sprayability is determined by the relation between power applied after stabilization and the total quantity of spraying. Quantities of spraying can be compared between apparatuses by providing a mode for inspecting the ability while fixing the power to the maximum level or the like independently of the automatic adjustment mode, so that whether or not the manufactured spray is non-defective can be determined on the basis of this information.

The spray preferably has the minimum number of operation switches for the user. Therefore, a simple spray has only a single operation switch for starting and stopping spraying, and no power fixing mode setting switch is preferably provided in this case so that the spray is user-friendly. When the spray has a supply voltage monitoring function for shifting to the fixed power mode when detecting prescribed fluctuation of the supply voltage, therefore, the apparatus can be set to the fixed power mode only when the same is inspected. No prescribed voltage fluctuation is allowed in practice, so that the apparatus can be prevented from erroneously shifting to the fixed power mode.

The spray employs large current for the spraying function leading to remarkable fluctuation of supply voltage or power supply noise particularly in the apparatus automatically adjusting the quantity of spraying as in the present invention, and hence erroneous shifting can be more reliably prevented by shifting to the fixed power mode when specific voltage fluctuation takes place before starting spraying immediately after power supply.

Figure 18:
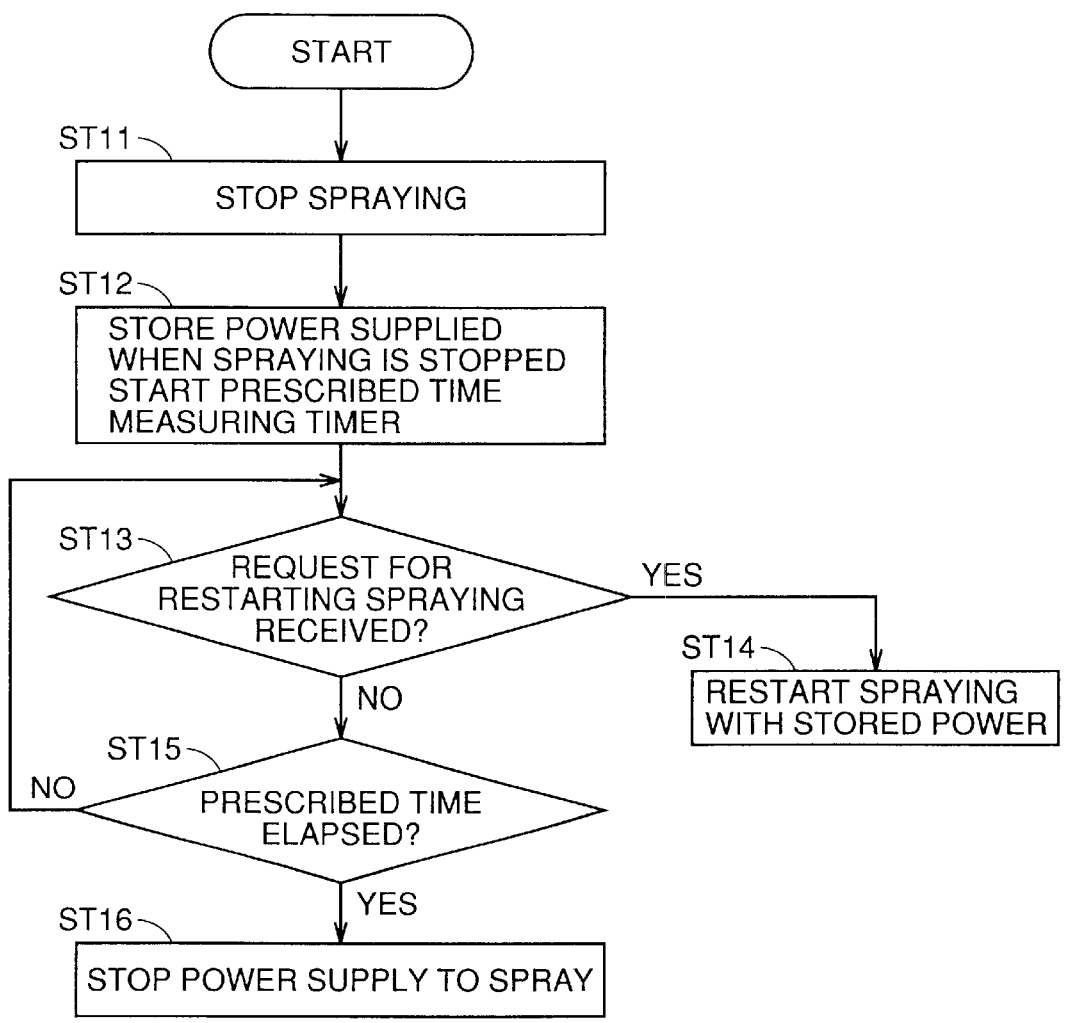

Depending on the way of using the spray, spraying may be temporarily interrupted. As to a medical inhaler, the patient may start or stop spraying in response to his breath. Thus, the amount of the spray liquid (liquid medicine for treatment or prevention) sprayed in vain can be reduced. In this case, it is effective to carry out processing of a flow chart shown in FIG. 18 as an inhaler according to another embodiment of the present invention, for restarting spraying after stopping spraying for a short prescribed time, with power supplied immediately before stopping spraying.

When spraying is stopped (ST11) in this case, the currently supplied power is stored and a timer for counting the prescribed time is started (ST12). A determination is made as to whether or not a request for restarting spraying is received (ST13). This determination is made by determining whether or not a switch for stopping or starting spraying is pushed. If the determination is of YES, the timer for counting the prescribed time is not yet up and hence spraying is restarted with the stored supply power (ST14). If no request for restarting spraying is detected at the step ST13, a determination is made as to whether or not the prescribed time has elapsed, i.e., whether or not the timer for counting the prescribed time is up (ST15) so that the process returns to the step ST13 to wait for the request for restarting spraying if the determination is of YES. If the timer is up with no request for restarting spraying at the step ST15, power supply to the spray is stopped (ST16).

While the power for the apparatus must be kept for storing the power supplied immediately before stopping spraying, power consumption can be reduced by cutting off the power for the apparatus after a lapse of the prescribed time since spraying may not be restarted with the power supplied immediately before stopping spraying.

When the spray liquid stored in the first storage part 20 is used up, no spray liquid is fed to the second storage part 30a but spraying is stopped and the spray is idled, and hence a device for monitoring the liquid level in the first storage part 20 is preferably provided. If a feeding determination part for the second storage part 30a determines that feeding is necessary after the liquid is repetitively fed from the first storage part 20 to the second storage part 30a by a prescribed number of times or for a prescribed time, however, operation of the spray may be stopped by determining that the spray liquid stored in the first storage part 20 has been entirely sprayed, so that the first storage part 20 may be provided with no liquid sensing part.

Figure 14:
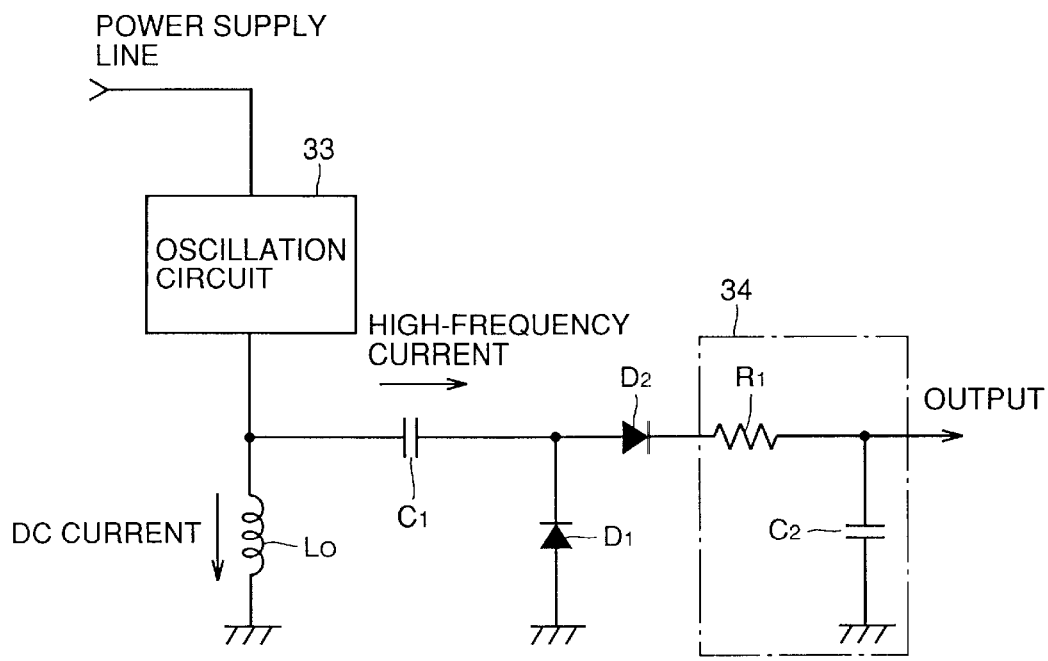

When an element such as a coil L0 having a high impedance in the oscillation frequency band is inserted into the side of a GND line in order to isolate a power supply part in a spray utilizing oscillation of an oscillator and having an automatic oscillation circuit utilizing the resonance characteristic of the oscillator as a driving circuit for the oscillator for forming a circuit for rectifying and smoothing a high-frequency current of an oscillation circuit 33, i.e., an oscillator driving frequency current with a circuit consisting of diodes D1 an D2 and converting the current to a voltage as shown in FIG. 14, the value of this voltage is substantially equal to energy used for spraying, and the quantity of spraying can be automatically adjusted by adjusting power supplied to a spray part so that the level of the voltage reaches a prescribed value.

When spraying is stopped, i.e., when oscillation of the circuit is stopped, no high-frequency current is present and hence no voltage is generated. When this voltage falls below the prescribed value, spraying is excessively attenuated or completely stopped to require an immediate countermeasure particularly in a medical inhaler, and it is effective to post the abnormality to the user by a display or a sound in this case.

If the spray breaks down by dropping or the like, the internal circuit may be exposed or the possibility of a danger such as a burn or a fire is presumed, and hence power supply to the oscillation circuit may be stopped when the breakdown is detected, so that safety for the user can be ensured.

While the liquid sensing electrodes 55 and 56 shown in FIGS. 7 and 17 have L shapes, shapes shown in FIGS. 19A to 19J or other ones are substitutionally employable for the liquid sensing electrodes 55, 56 and 57.

Figure 20A:
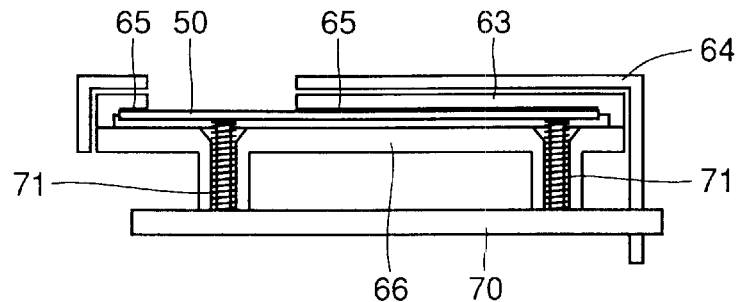
Figure 20B:
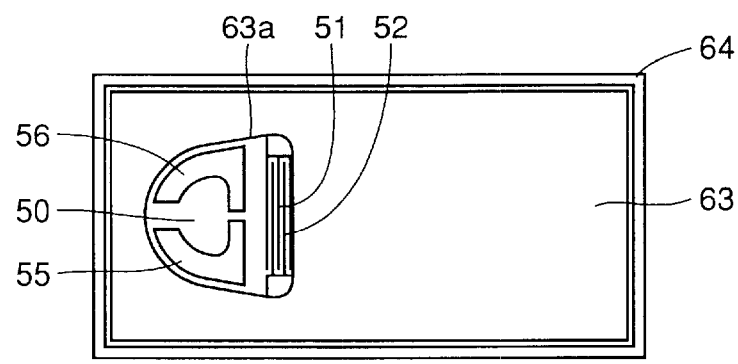
Figure 20C:
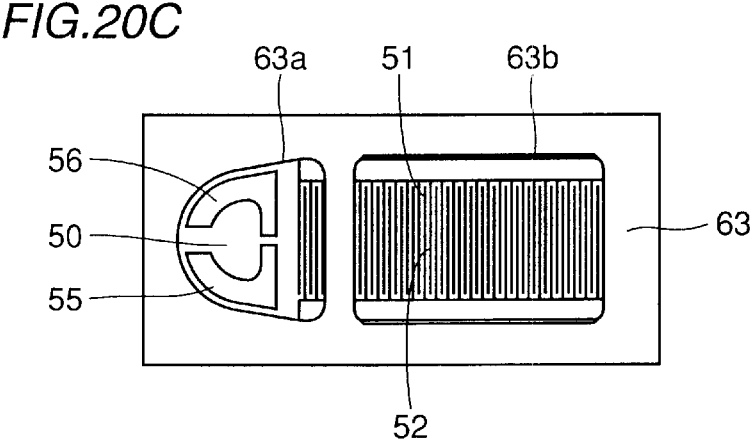
Figure 20D:
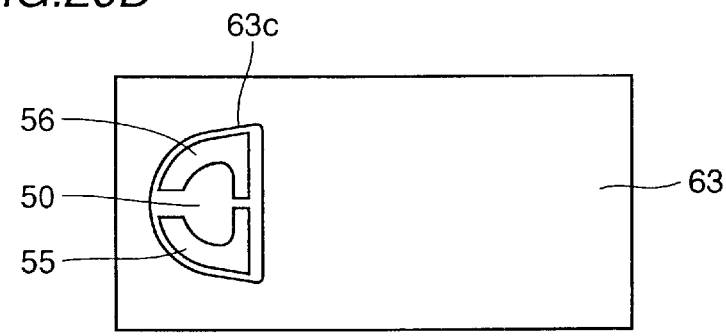

FIGS. 20A to 20D are diagrams showing other structures of mounting the piezoelectric element employable for the inhaler according to the embodiment of the present invention. FIG. 20A is a sectional view showing the piezoelectric element 50 integrally held on a piezoelectric element holding part 63 with an adhesive 65. The interdigital electrodes 51 and 52 and the liquid sensing electrodes 55 and 56 are formed on the surface of the piezoelectric element 50 opposite to the side bonded to the piezoelectric element holding part 63. The piezoelectric element 50 is placed on a base 66 while directing the electrodes 51, 52, 55 and 56 downward, and the electrodes 51, 52, 55 and 56 are connected to the circuit part of the substrate 70 by the conductive elastic bodies 71. The upper surface of the piezoelectric element 50 is covered with a shielding body 64 of a metal. Referring to FIGS. 20B, 20C and 20D showing some examples of the piezoelectric element holding part 63 as viewed from above, FIG. 20B illustrates a hole part 63a showing the liquid sensing electrodes 55 and 56 and a part of the interdigital electrode 51, FIG. 20C illustrates a hole part 63a showing the liquid sensing electrodes 55 and 56 and parts of the interdigital electrodes 51 and 52 and another hole part 63b showing most parts of the interdigital electrodes 51 and 52, and FIG. 20D illustrates a hole 63c through which only the liquid sensing electrodes 55 and 56 can be visually recognized from above.

A metal or ceramic is used as the material for the piezoelectric element holding part 63. When the atomized liquid adheres to the peripheral holding part, the holding hardly absorbs ultrasonic vibration through the liquid due to the employment of the aforementioned material, so that atomization efficiency can be improved. Alternatively, heat-resistant resin may be employed as the material for the piezoelectric element holding part 63. When the temperature is increased by absorbing ultrasonic energy, the piezoelectric element holding part 63 can be prevented from deformation or the like due to employment of the heat-resistant resin.

It is possible to reliably hold the piezoelectric element 50 by a simple method by bonding the piezoelectric element 50 to the piezoelectric element holding part 63 with the adhesive. The piezoelectric element holding part 63 may be coated with a water-repellent material. The absorptivity for ultrasonic waves can be reduced and spots of the liquid can be readily removed by improving water repellency.

The interdigital electrode 51 is partially or entirely covered with the piezoelectric element holding part 63 shown in FIGS. 20B, 20C or 20D, whereby the liquid can be prevented from adhering to the interdigital electrode 51 and remarkably damping vibration.

The metal shielding body 64 is connected to a low impedance part of the piezoelectric element driving circuit of the substrate 70.

The metal shielding body 64 may consist of the piezoelectric element holding part 63.

INDUSTRIAL AVAILABILITY

In the spray according to the present invention, as hereinabove described, the power supplied to the spray part is so adjusted that the spray liquid is fed to the storage part of the spray part, holding the liquid medicine immediately before the liquid medicine is sprayed, at a prescribed interval, whereby a spray capable of automatically adjusting the quantity of spraying per dose to a constant level can be provided.

What is claimed is:

1. A spray comprising a first storage part and a second storage part for storing a spray liquid, a spray part spraying the spray liquid stored in said second storage part, a feeding part feeding a constant quantity of spray liquid from said first storage part to said second storage part, a liquid sensing part detecting presence/absence or increase/decrease of the spray liquid in said second storage part and a feeding determination part for determining whether or not said second storage part requires feeding on the basis of an output from said liquid sensing part, for automatically adjusting the quantity of spraying by adjusting power supplied to the spray part so that the spray liquid is fed to said second storage part at a prescribed interval.

2. The spray according to claim 1, wherein said spray part is formed by a piezoelectric element and piezoelectric element driving means, said second storage part is formed by part of the surface of said piezoelectric element and said spray comprises a liquid sensing circuit having an electrode for liquid sensing on a surface of said second storage part opposite to said piezoelectric element for sensing presence/absence or increase/decrease of the liquid in the storage part on the basis of an output from the liquid sensing electrode.

3. The spray according to claim 2, wherein said liquid sensing circuit forms an oscillation circuit utilizing a resonance characteristic specifically decided from the size of said piezoelectric element, the shape of said liquid sensing electrode and the like for sensing the liquid by detecting presence/absence of oscillation or change of the oscillation frequency.

4. The spray according to claim 2, wherein a plurality of said liquid sensing electrodes are arranged in parallel in a direction perpendicular to a direction where the liquid decreases so that the liquid is sensed by detecting change of electrostatic capacitance across the electrodes.

5. The spray according to claim 2, wherein said liquid sensing circuit is formed by a frequency output, and a piezoelectric driving frequency band and a liquid sensing circuit output frequency band are separated from each other.

6. The spray according to claim 5, wherein said liquid sensing circuit output frequency band is sufficiently lowered with respect to said piezoelectric element driving frequency band.

7. The spray according to claim 6, wherein a low-pass filter circuit is added to an output of said liquid sensing circuit for cutting noise of the piezoelectric element driving frequency band.

8. The spray according to claim 2, automatically adjusting the quantity of spraying per unit time by periodically stopping driving the piezoelectric element and adjusting driving power for the piezoelectric element on the basis of an output from the liquid sensing circuit during the stop period.

9. The spray according to claim 2, employing pulse control for turning on/off driving power to the piezoelectric element for automatically adjusting the quantity of spraying per unit time on the basis of an output from the liquid sensing circuit during the OFF period.

10. The spray according to claim 8, wherein said spray is employed for inhalation, and the driving power to said piezoelectric element is off for a period of not more than 15 ms.

11. The spray according to claim 2, wherein said liquid sensing electrode is slightly inclined from vertical arrangement with respect to the direction of an oscillatory wave of the piezoelectric element generated by driving the piezoelectric element.

12. The spray according to claim 2, wherein an electrode to be connected to a fixed potential having a low impedance is arranged on the surface of said second storage part opposite to the piezoelectric element independently of the electrode for liquid sensing.

13. The spray according to claim 2, wherein at least one of said liquid sensing electrode is connected to a fixed potential having a low impedance.

14. The spray according to claim 12, wherein said electrode connected to the fixed potential is slightly inclined from vertical arrangement with respect to the direction of an oscillatory wave of the piezoelectric element generated by driving the piezoelectric element.

15. The spray according to claim 1, wherein said spray is employed for inhalation, and the quantity of the spray liquid fed to said second storage part per dose is not more than 100 μl.

16. The spray according to claim 15, wherein the initial value of power supplied to the spray part is set to the maximum level.

17. The spray according to claim 1, having a power fixing mode for inspecting sprayability.

18. The spray according to claim 17, having a supply voltage monitoring function for shifting to the power fixing mode when prescribed supply voltage fluctuation is detected.

19. The spray according to claim 18, shifting to the power fixing mode when specific supply voltage fluctuation is detected before starting spraying immediately after power supply to the apparatus.

20. The spray according to claim 1, storing power supplied to the spray part immediately before spraying is stopped within a prescribed time once spraying is stopped, for starting spraying with the stored power when spraying is restarted within the prescribed time.

21. The spray according to claim 20, storing the power supplied to the spray part immediately before spraying is stopped by holding a body power source within the prescribed time and completely disconnecting the power source after a lapse of the prescribed time.

22. The spray according to claim 1, determining that the spray liquid in said first storage part runs out and cutting off power supply to said spray part when said feeding determination part of said second storage part determines that feeding is necessary even if said first storage part repetitively feeds the liquid to said second storage part by a prescribed number of times or for a prescribed period.

* * * * *